United States Patent [19]

Linovitz et al.

[11] Patent Number: 5,026,375
[45] Date of Patent: Jun. 25, 1991

[54] SURGICAL CUTTING INSTRUMENT

[75] Inventors: Raymond J. Linovitz, Rancho Santa Fe; Randy J. Kesten, Redwood City, both of Calif.

[73] Assignee: Origin Medsystems, Inc., San Mateo, Calif.

[21] Appl. No.: 427,180

[22] Filed: Oct. 25, 1989

[51] Int. Cl.⁵ .............................. A61F 5/04; B26B 9/00
[52] U.S. Cl. ......................................... 606/79; 30/349
[58] Field of Search ....................... 606/79, 80, 82, 83, 606/84, 98, 99, 100, 104, 105; 30/349, 356, 357, 392, 514, 517, 518, 519, 366

[56] References Cited

U.S. PATENT DOCUMENTS

| | | | |
|---|---|---|---|
| 460,903 | 10/1891 | Woodward | 606/79 |
| 1,493,240 | 5/1924 | Bohn | 606/79 X |
| 3,752,161 | 8/1973 | Bent | 606/79 X |
| 3,902,498 | 9/1975 | Niederer | 30/130 |
| 4,201,213 | 5/1980 | Townsend | 606/79 |
| 4,368,734 | 1/1983 | Banko | 606/79 |
| 4,777,948 | 10/1988 | Wright | 606/83 |

*Primary Examiner*—Mickey Yu
*Assistant Examiner*—Michael Brown
*Attorney, Agent, or Firm*—Majestic, Parsons, Siebert & Hsue

[57] ABSTRACT

A bone-cutting surgical implement, commonly called a rongeur, has a pistol-like grip with a finger controlled lever in pivotal engagement with the handle. Extending from the handle is a rod defining an upward facing, longitudinal keyway. The rod also has an upwardly angularly protruding jaw facing backward along the rod. A second rod is in slidable engagement with the first rod by a key disposed in the keyway. The arrangement constrains the slidable rod to rectilinear motion along the first rod. At an extremity of the slidable rod proximal to the handle, the slidable rod is pivotally connected to the lever. By moving the lever an operator is able to move the slidable rod along the fixed rod. A replaceable, disposable jaw is releasably coupled to a distal extremity of the slidable rod and faces the end jaw of the first rod. The replaceable jaw is also guided by the keyway defined by the first rod. By moving the lever, an operator is able to move the replaceable jaw between two extremities, one extremity abuts the other jaw and the second extremity is adjacent but beyond an opening which allows a key connected to the replaceable jaw to be inserted into the keyway.

9 Claims, 1 Drawing Sheet

U.S. Patent
June 25, 1991
5,026,375
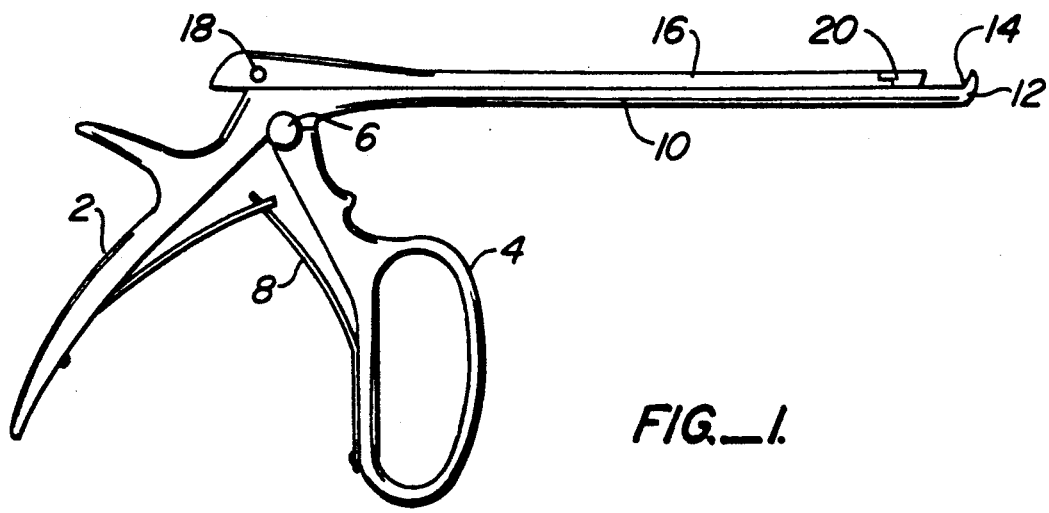
FIG._1.
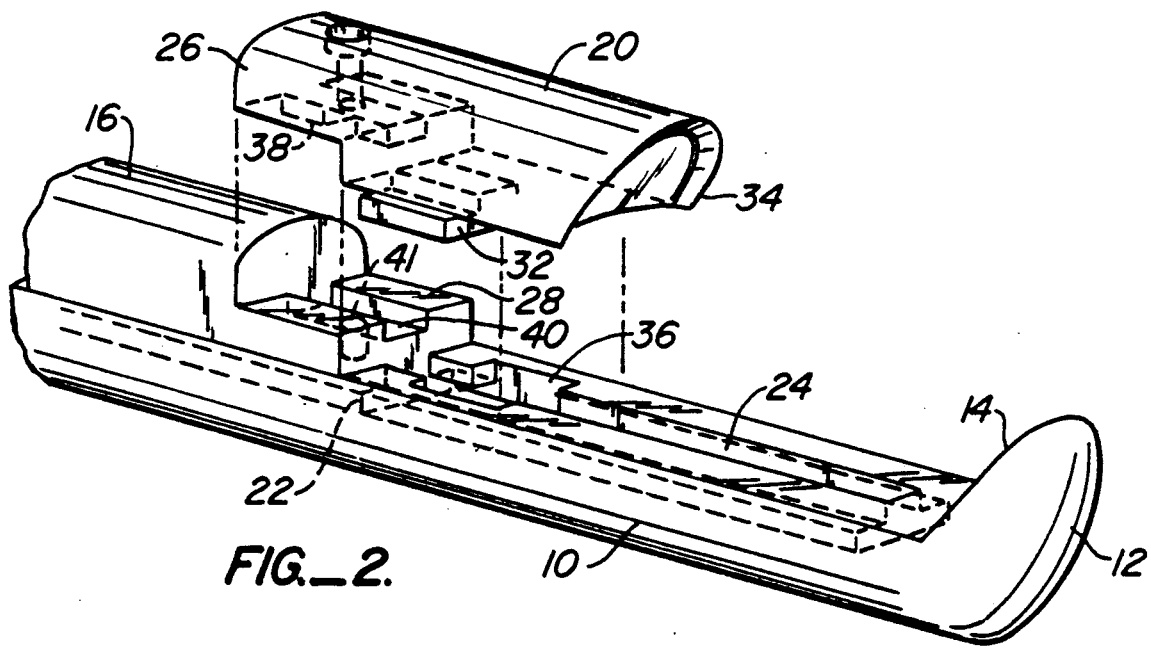
FIG._2.
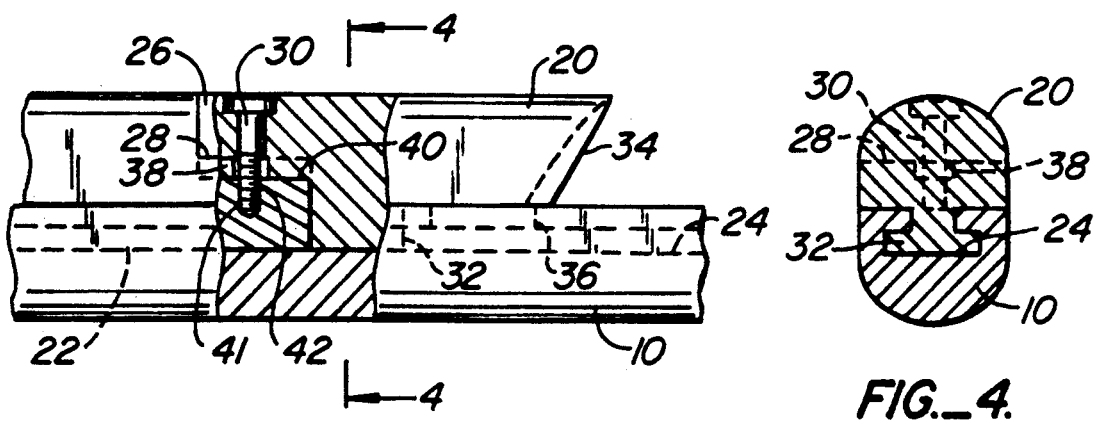
FIG._3.
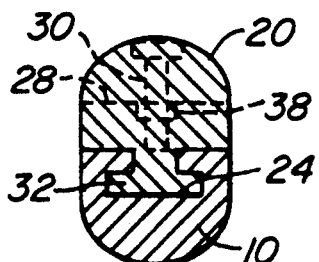
FIG._4.

SURGICAL CUTTING INSTRUMENT

BACKGROUND OF THE INVENTION

This invention relates to surgical cutting instruments and in particular rongeurs and the like with replaceable cutting tips.

Rongeurs have been used for many years as surgical cutting implements, particularly to cut bone. To be so used, at least one of the jaws of a rongeur must have a very fine cutting edge. In the course of a surgical procedure, however, the jaws can become dull making the implement therefore no longer usable. A dulled cutting edge can cause a portion of the instrument to buckle thereby destroying the instrument. Moreover a dulled instrument is a danger to the patient for several reasons. For example, a dull instrument can cause tissue tearing and it can cause an increase in the operating time both of which can result in increased blood loss and further expense to the patient.

It is conventional practice to either have the cutting edges sharpened or dispose of such implements with dulled edges. In either case great expense is incurred. The cutting edges can typically be sharpened only four times before the jaws no longer meet properly in which case the instrument must be replaced. Currently replacement cost for a single instrument is $500 to $600 dollars, and the useful life of such an instrument is only one to one and one-half years. Since it is customary to use three to four different size rongeurs during a single operation, replacement of an entire set is a significant expense.

Heretofore, an economically practical disposable cutting edge for such implements to make them readily reusable has not been available. This invention presents an economically attractive alternative which makes such implements readily reusable but at a cost much less than is typically required to resharpen them.

Wright U.S. Pat. No. 4,777,948 presents a pistol-like rongeur with a fixed hollow barrel with a slidable rod therein. A forward end of the rod extends beyond the barrel and is up-turned to provide a distal jaw, i.e., a shoulder to oppose a proximal jaw which is a replaceable tube, basically an extension of the barrel. The forward edge of the tube is a cutting edge. The rearmost portion of the tube is clamped to the end of the barrel by a chuck-like device comprising threaded fingers which can be increasingly tightened together by a frusto-conical nut.

Townsend U.S. Pat. No. 4,201,213 presents another barrel and rod in slidable arrangement. In this case, however, the rod is fixed and the barrel is slidable. The forward end of the rod is once again angularly up-turned to form a distal jaw, but this one has an inward facing cutting edge. Opposing that is an outwardly facing cutting edge on an "insert" 16. The inventor describes the insert as not being necessary but is there to "provide additional surface area to the jaw for increased strength . . . " (Col. 3, lines 44–59).

Banko U.S. Pat. No. 4,368,734 presents another surgical instrument but this one is used to perform operations on eyes. It has a fixed outer member 18 with a down-turned end to act as a pointed distal jaw. It also has an inner tube disposed within the outer member, the forward edge of which is the cutting edge of a proximal jaw. Both appear to be replaceable.

Niederer U.S. Pat. No. 3,902,498 presents another surgical instrument similar at its operational tip to the Wright device. It has a fixed barrel with a slidable rod disposed therein. The slidable rod has an up-turned forward end to function as a distal jaw which opposes a circular cutting edge at the forward end of the barrel. As in the Wright patent, the forward end of the barrel, that is the cutting piece, is essentially an extension of the barrel. The cutting piece is replaceable but the inner rod does not appear to be disposable.

Woodward U.S. Pat. No. 460,903 presents a fruit picker. It has a fixed flat bar with two opposed laterally inward slots such that the end of the bar appears to be arrowhead-shaped. The stem of the fruit being picked is inserted into one of these slots. A superior blade with a forward cutting edge slides axially upon the fixed bar to shear the stem. An inferior blade with a blunt forward edge moves with the shearing blade to press the stem against a shoulder formed by the fixed bar. Thus, the device not only shears the fruit from its stem, but continues to grasp the sheared fruit by the cut stem.

Other advantages and attributes of this invention will be hereinafter discussed or will be readily discernible from a reading of the text hereinafter.

SUMMARY OF THE INVENTION

This invention presents a pistol-like surgical cutting instrument with a handle, an elongated member having a fixed jaw protruding angularly therefrom at an extremity distal from the handle, the jaw facing backward along the member. A slidable jaw faces in opposition to the elongated member jaw and is releasably constrained to slide in rectilinear motion along the elongated member between an extremity whereat the slidable jaw abuts the fixed jaw and an extremity where it is suitably spaced from the other jaw. The suitability of the space is determined by the objects to be cut by the instrument and the environment in which the instrument is required to operate. The spacing must also allow for engagement and disengagement of the slidable jaw with the elongated member. The implement further comprises means for moving the constrained slidable jaw to change the spacing between the jaws and apply a force to an object disposed between the jaws. As expressed above, a factor in determining the suitability of the extreme spacing between the jaws is the dimensional range of the objects to be cut.

The sliding jaw preferably has a releasably mounted, disposable cutting tip. Thus a sharp cutting edge or tip will always be available to the surgeon without replacement of the entire tool or sending it out for sharpening. This results in considerable time and cost savings.

An object of this invention is to provide a replaceable cutting edge for surgical cutting implements such as rongeurs and the like, which can be replaced both quickly and easily.

Another object of this invention is to provide a means whereby rongeurs and the like can be made reusable for much less cost than replacing them.

A further object of this invention is to provide a means for replacing the cutting edge of the cutting jaw of a rongeur at much less cost than sharpening same.

BRIEF DESCRIPTION OF THE DRAWINGS

FIG. 1 is a side elevation view of a typical instrument incorporating the replaceable tip;

FIG. 2 is an exploded perspective view of the distal end of the implement.

FIG. 3 is a side elevation view of the distal end of the implement, partially cut away; and FIG. 4 is a sectional view taken on line 4—4 of FIG. 3.

DESCRIPTION OF THE PREFERRED EMBODIMENT(S)

Referring to FIG. 1, a surgical cutting implement is illustrated as having a pistol-like handle 2 which fits into the hollow of a user's hand and allows the user to manipulate a lever 4 by his or her fingers. The lever is pivotally affixed to the handle by a pivot pin 6 which allows the free end of the lever 4 to be pivoted toward and away from handle 2. A biasing spring 8 urges the free end of the lever away from the handle.

Angularly projecting from an upper end of the handle 2, and preferably integral therewith, is an elongated member illustrated as a fixed rod 10, fixed in relation to the handle. At an extremity of the fixed rod 10, distal from the handle 2 is a jaw 12 projecting from the rod with a face 14 facing backward along the rod 10 toward the handle. As will be seen, the face 14 is a cutting surface, a surface against which the cutting edge of an opposing jaw is pressed to cut an object therebetween. As illustrated the jaw 12 projects upward and the face 14 is inclined away from the direction of the handle, however this invention works equally as well with a downwardly projecting jaw and/or with an inclined or normal face. A second rod 16 atop the elongated member or fixed rod is in slidable engagement with the fixed rod 10. The slidable rod 16 is constrained as will be explained to reciprocal rectilinear movement along the top of the fixed rod 10.

At an end of the slidable rod 16 proximal to the handle, the slidable rod is in pivotal engagement with a portion of the lever 4 extending beyond the pivot 6. Said pivotal engagement is by means of a pivot pin 18. This pivotal arrangement between the lever 4 and the slidable rod 16 allows a user to move the second rod 16 back and forth across the fixed rod 10 by movement of the lever 4. At an extremity of the slidable rod 16 distal from the handle is disposed a replaceable, and preferably disposable, jaw piece 20. As will be explained, the jaw piece is releasably coupled to said extremity of the slidable rod 16. In operation, the combination of the lever 4 and the slidable rod 16 are used to change the spacing between the two jaws and apply a force to an object disposed between the jaws.

Referring to FIGS. 2, 3 and 4, as illustrated the slidable rod 16 has a generally T-shaped, longitudinal projection or key 22 along its underside. (The projection 22 would be along the rod's upper side if jaw 12 projected downwardly from the fixed rod 10.) In the assembled form of the implement as shown in FIG. 1, the key 22 is disposed in, and travels through, a generally T-shaped keyway 24 defined by the fixed rod 10 along its side facing the slidable rod 16. By this arrangement, the slidable rod 16 is constrained to rectilinear motion along the top side of first rod 10.

A replaceable, and preferably disposable, jaw 20 is releasably coupled to the distal end of the slidable rod 16. A rearward projecting flange 26 of the replaceable jaw 20 is joined by a securing coupling pin 30 illustrated as a screw to a mating flange 28 projecting forward from the slidable rod's distal end. Screw 30 engages in threaded bore 41 defined by flange 28 and is self-locking in a well known manner by an elastomeric insert 42 in the screw threads as illustrated in FIG. 3. The jaw piece 20 also has a generally T-shaped key 32 for travel in the keyway 24. The key 32 of the replaceable jaw piece 20 is inserted into and removed from the keyway 24 by means of a passageway 36 defined by the first rod 10 adjacent the position of the distal extremity of the slidable rod 16 at said rod's furthest rearward extent. At the interface of the mating flanges, 26 and 28, is a tongue and groove joint for added strength. A discontinuous rib-like tongue 38 projects from the former flange 26 and fits exactly into a groove 40 defined by the latter flange 28. The tongue 38 is discontinuous to accommodate passage of the coupling pin 30 therethrough. Preferably the head of coupling pin 30 is countersunk and flush with the slidable rod to avoid injury to a patient. Likewise and for the same reason it is preferable that the outer surfaces of the flange joint (between flanges 26 and 28) be a smooth continuation of the corresponding surfaces of the slidable rod. This joint arrangement reduces stress in use of the rongeur and increases strength.

In operation, a jaw piece 20 is removed by first moving the slidable rod 16 by action of the lever to its rearmost position. At this position the space between the two jaws is greatest and the angle between the handle 2 and the lever 4 is the greatest. Also the passageway 36 is accessible. The securing coupling pin 30 is then removed and the jaw piece is lifted upward, the key 32 of the jaw piece 20 passing through the opening 36. A new jaw piece 20 can then be inserted by reversing the process.

Referring to FIG. 2, the cutting or front face 34 of the jaw piece 20 is angled to match the inclination of face 14 of the opposing jaw 12. Preferably, the face 34 is concave forming a sharp cutting edge at the margin of the face.

The replaceable, disposable cutting jaw tip 20 will significantly extend the lifetime of a rongeur, resulting in considerable cost savings in an operating room where three to four different size rongeurs are needed for each operation. The relatively inexpensive disposable cutting tip can be removed and replaced quickly and easily, and allows surgeons to always use a sharp cutting edge, increasing efficiency and safety of operations. Rongeurs do not need to be replaced or sent out for sharpening, which would result in loss of use of the rongeur during the sharpening time.

The foregoing description and drawings were given for illustrative purposes only, it being understood that the invention is not limited to the embodiments disclosed, but is intended to embrace any and all alternatives, equivalents, modifications, derivatives and rearrangements of elements falling within the scope of the invention as defined by the following claims.

We claim:

1. A surgical cutting implement comprising:
   (a) a fixed elongated member having a first jaw means projecting therefrom at an end, said first jaw means having a cutting surface which faces back along said elongated member,
   (b) a slidable member slidably engaged with the fixed member, said slidable member being confined to rectilinear motion along the fixed member to a range of motion,
   (c) a second jaw means having a cutting edge face, the second jaw means being releasably affixed to an end of the slidable member for opposing the first jaw means, the second jaw means being adapted to be squarely closed against the first jaw means at one extremity of the range of motion of the slidable member, (d) means for moving the slidable member in relation to the fixed member to change the spacing between the first and second jaw means and apply a force to an object disposed between the first and second jaw means, (e) a rigid joint means for affixing said second jaw means to the end of the slidable member, (f) a key projecting from said second jaw means which is held by and travels in a keyway defined by the fixed member, and (g) an opening in the fixed member through which the key can be inserted into and removed from the keyway, wherein said rigid joint means comprises a coupling means, said second jaw means and said slidable member and said second jaw means having aligned bores through which said coupling means projects to releasably couple said second jaw means to said slidable member.

2. The implement according to claim 1, wherein said coupling means comprises a screw, said bore in said slidable member comprising a threaded bore for threaded engagement with said screw.

3. A surgical cutting implement comprising:

(a) a fixed elongated member having a first jaw means projecting therefrom at an end, said first jaw means having a cutting surface which faces back along said elongated member, (b) a slidable member slidably engaged with the fixed member, said slidable member being confined to rectilinear motion along the fixed member to a range of motion, (c) a second jaw means having a cutting edge face, the second jaw means being releasably affixed to an end of the slidable member for opposing the first jaw means, the second jaw means being adapted to be squarely closed against the first jaw means at one extremity of the range of motion of the slidable member, (d) means for moving the slidable member in relation to the fixed member to change the spacing between the first and second jaw means and apply a force to an object disposed between the first and second jaw means, (e) a rigid joint means for affixing said second jaw means to the end of the slidable member, (f) a key projecting from said second jaw means which is held by and travels in a keyway defined by the fixed member, and (g) an opening in the fixed member through which the key can be inserted into and removed from the keyway, said joint means comprising a flange joint and a tongue and groove joint, said flange joint comprising two overlapping flanges, one each projecting from said second jaw means and said slidable member, and a coupling means, said second jaw means, flange and slidable member flange having aligned bores through which said coupling means projects to releasably couple said jaw means to said slidable member, and wherein said coupling means comprises a screw, said bore in said slidable member comprising a threaded bore for threaded engagement with said screw.

4. A surgical cutting implement comprising:

(a) a fixed elongated member having a first jaw means projecting therefrom at an end, said first jaw means having a cutting surface which faces back along said elongated member, (b) a slidable member slidably engaged with the fixed member, said slidable member being confined to rectilinear motion along the fixed member to a range of motion, (c) a second jaw means having a cutting edge face, the second jaw means being releasably affixed to an end of the slidable member for opposing the first jaw means, the second jaw means being adapted to be closed against the first jaw means at one extremity of the range of motion of the slidable member, (d) means for moving the slidable member in relation to the fixed member to change the spacing between the first and second jaw means and apply a force to an object disposed between the first and second jaw means, (e) a rigid joint means for affixing said second jaw means to the end of the slidable member, (f) a key projecting from said second jaw means which is held by and travels in a keyway defined by the fixed member, and (g) an opening in the fixed member through which the key can be inserted into and removed from the keyway.

5. The implement according to claim 4 wherein the joint means comprises a flange joint and a tongue and groove joint.

6. The implement according to claim 5 wherein the flange joint comprises two overlapping flanges, one each projecting from said jaw means and said slidable member, and a coupling means, said jaw means flange and slidable member flange having aligned bores through which said coupling means projects to releasably couple said second jaw means to said slidable member.

7. The implement according to claim 6, wherein said coupling means comprises a screw, said bore in said slidable member comprising a threaded bore for threaded engagement with said screw.

8. The implement according to claim 4, wherein said joint means comprises a coupling means, said second jaw means and slidable member having aligned bores through which said coupling means projects to releasably couple said second jaw means to said slidable member.

9. The implement according to claim 8, wherein said coupling means comprises a screw, said bore in said slidable member comprising a threaded bore for threaded engagement with said screw.

* * * * *